United States Patent
Bönsch et al.

(10) Patent No.: US 6,534,678 B1
(45) Date of Patent: Mar. 18, 2003

(54) PROCESS FOR PRODUCING TARTARIC ACID FROM A RAW MATERIAL CONTAINING POTASSIUM HYDROGENTARTRATE

(75) Inventors: Rudolf Bönsch, Nackenheim (DE); Dieter Stein, Wiesbaden (DE); Klaus Erb, Goslar (DE)

(73) Assignees: Metallgesellschaft Aktiengesellschaft, Frankfurt am Main (DE); Spezial Chemie Leuna GmbH & Co. KG, Leuna (DE)

( * ) Notice: Subject to any disclaimer, the term of this patent is extended or adjusted under 35 U.S.C. 154(b) by 0 days.

(21) Appl. No.: 09/303,975

(22) Filed: May 3, 1999

(30) Foreign Application Priority Data

May 4, 1998 (DE) .......................... 198 19 884

(51) Int. Cl.[7] .................. C07C 51/42; C07C 59/255
(52) U.S. Cl. ...................... 562/585; 562/580
(58) Field of Search ................. 562/580, 585

(56) References Cited

U.S. PATENT DOCUMENTS

| 1,945,246 A | | 1/1934 | Witzel ................ 260/122 |
| 2,303,604 A | | 12/1942 | Braun ................ 260/536 |
| 2,470,841 A | * | 5/1949 | Barch ................ 562/402 |
| 3,498,795 A | * | 3/1970 | Walter ................ 426/442 |
| 3,998,878 A | * | 12/1976 | Hearon et al. ........... 562/577 |
| 4,092,220 A | * | 5/1978 | Tsurumi et al. .......... 435/145 |
| 4,656,303 A | * | 4/1987 | Kurono et al. ........... 558/354 |
| 4,781,809 A | * | 11/1988 | Falcone, Jr. ............ 204/537 |
| 4,798,131 A | * | 1/1989 | Ohta et al. ............. 99/277.2 |
| 4,889,743 A | * | 12/1989 | Tazawa et al. ........... 426/495 |

FOREIGN PATENT DOCUMENTS

| CZ | 126128 | * | 2/1968 |
| DE | 264 005 | | 9/1913 |
| DE | 12 77 215 | | 9/1968 |

* cited by examiner

Primary Examiner—Alan L. Rotman
Assistant Examiner—Taylor V. Oh
(74) Attorney, Agent, or Firm—Norris McLaughlin & Marcus

(57) ABSTRACT

Process for producing tartaric acid from a raw material whose dry matter comprises at least 5 wt% potassium hydrogentartrate wherein the raw material containing potassium hydrogen tartrate (KHT) is mixed with aqueous potassium hydroxide solution in a first reaction stage, where KHT is virtually completely reacted to form dipotassium tartrate (DKT), the aqueous solution containing DKT is then mixed with added acid in a precipitation stage at a pH value of 2.0 to 5.0, to produce a suspension containing crystallized KHT; crystallized KHT is then separated from the suspension, washed with water, and there is produced a solution at least 80 wt-% saturated with KHT and then the potassium is removed, to obtain an aqueous tartaric acid product solution, from which water is then at least partly removed.

6 Claims, 1 Drawing Sheet

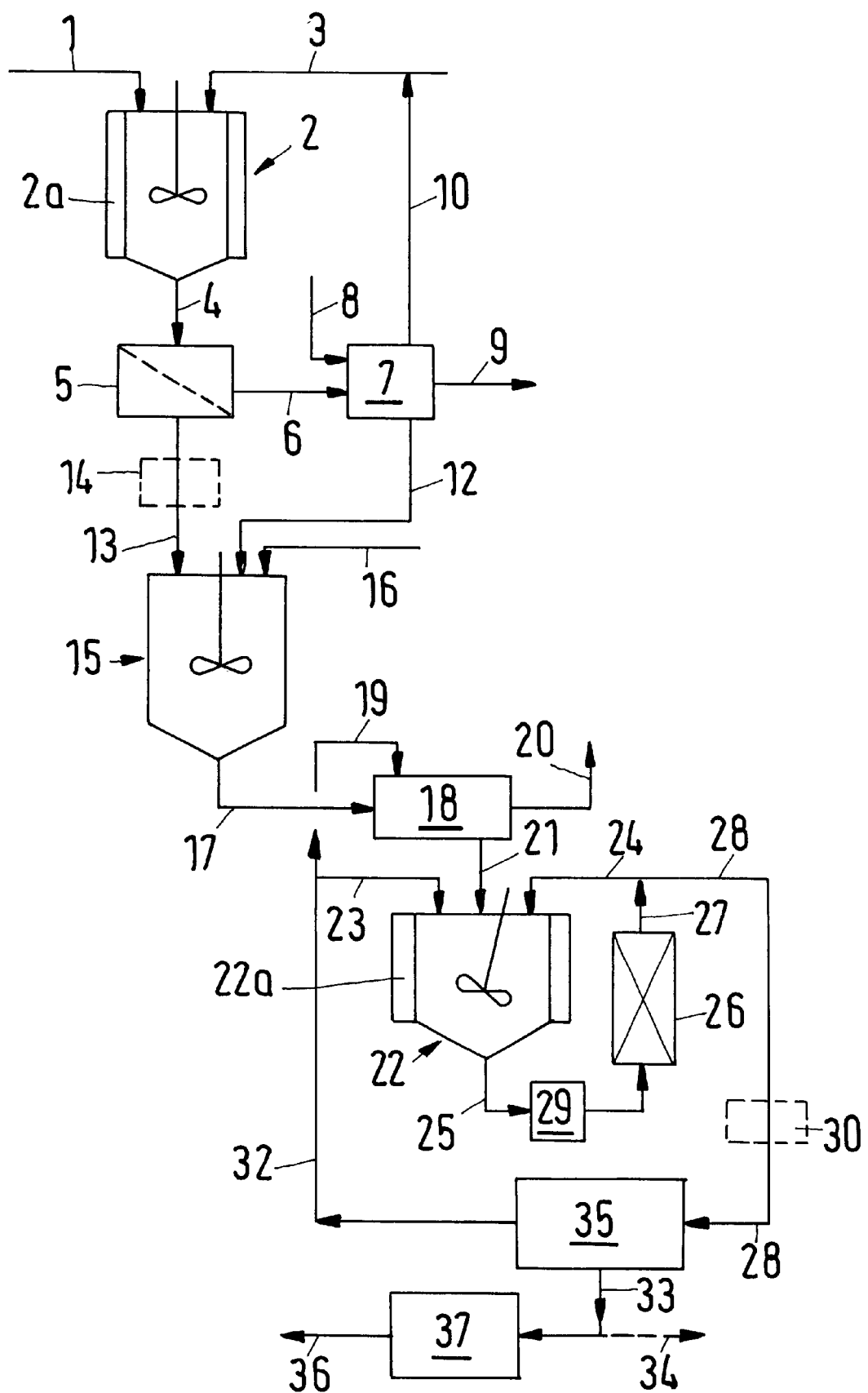

PROCESS FOR PRODUCING TARTARIC ACID FROM A RAW MATERIAL CONTAINING POTASSIUM HYDROGENTARTRATE

BACKGROUND OF THE INVENTION

This invention relates to a process of producing tartaric acid from a raw material whose dry matter comprises at least 5 wt-% potassium hydrogentartrate (KHT). As raw material, there may for instance be used wine yeast and/or tartar, which are obtained during the production of wine. Preferably, the KHT content of the raw material, based on dry matter, is at least 10 wt-%.

SUMMARY OF THE INVENTION

It is the object underlying the invention to produce a purified tartaric acid, which may also be useful for foodstuffs, in an environmentally beneficial and inexpensive way. In accordance with the invention this is achieved in
a) that in a first reaction stage the raw material is mixed with aqueous potassium hydroxide solution, and KHT is virtually completely reacted to form dipotassium tartrate (DKT),
b) that from the first reaction stage there is withdrawn a first aqueous solution containing DKT, impurities are removed, and in a precipitation stage the first solution is mixed with added acid at a pH value of 2.0 to 5.0, and a suspension containing crystallized KHT is produced,
c) that crystallized KHT is separated from the suspension, washed with water, and there is produced a second aqueous solution saturated with KHT for at least 80 wt-% and
d) that from the second aqueous solution potassium is removed, an aqueous tartaric acid solution is produced, and from the tartaric acid solution water is at least partly removed.

DETAILED DESCRIPTION

Tartaric acid has the empirical formula $H_6C_4O_6$, potassium hydrogentartrate is $KH_5C_4O_6$ and dipotassium tartrate is $K_2H_4C_4O_4$. In the first reaction stage a) KHT is reacted with KOH to form DKT ($K_2H_4C_4O_6$) plus water, where preferably a pH value of 7 to 8 is employed. DKT has a much better solubility in water than KHT.

The first aqueous solution containing DKT is mixed with added acid in the precipitation stage, where the poorly soluble KHT is formed. It is recommended to use tartaric acid as acid, when the introduction of foreign substances should rather be avoided. It is, however, very well possible to employ for instance $H_2SO_4$ or HCl instead of tartaric acid, and to remove the sulfate or chloride ions from the process at another point.

The process is likewise suited for processing yeast-containing raw material, which is charged to the first reaction stage a). From the first stage, a first solution containing DKT and yeast is withdrawn, and the yeast-containing sludge is separated, for instance by microfiltration, ultrafiltration or by means of one or several centrifuges. Embodiments of the process will be explained by means of the drawing.

BRIEF DESCRIPTION OF THE DRAWING

The drawing represents a flow diagram of the process.
The raw material containing KHT is supplied via line 1 and charged into a stirred tank 2. In the following it is assumed that the raw material also contains yeast. Aqueous KOH solution comes from line 3. The liquid in the tank 2 is expediently heated to about 60 to 80° C., and for this purpose the tank 2 is equipped with a heating jacket 2a. KOH is added in such an amount that KHT is completely reacted to form DKT. The pH value of the liquid in the tank 2 usually is about 7 to 8. The solution withdrawn from the tank 2 via line 4 is also referred to as "first aqueous solution". The solution is charged to a filtration 5, in order to separate a yeast sludge which is withdrawn via line 6 and supplied to a washing stage 7. Washing water comes from line 8.

Via line 9, a washed yeast is withdrawn, which may for instance be employed as fodder. The used washing water is divided, and the first part is supplied through line 10 to line 3 and in this way back to the tank 2. The residual used washing water is withdrawn via line 12 and charged into a precipitation tank 15.

The filtrate, which is withdrawn from the filter 5 via line 13, above all contains DKT and as impurities for instance sugar, alcohol, various acids and dyestuffs. It may be expedient to pass this solution first through a decoloration 14, which is usually designed as activated carbon fixed bed. However, the decoloration may alternatively be effected at another point of the process.

To the precipitation tank 15 the solution from line 13, the used washing water from line 12 and an acid are supplied, which acid is supplied via line 16. This acid may for instance be tartaric acid. The acid converts the DKT virtually completely to KHT. In the precipitation tank 15 relatively low temperatures are ensured, preferably in the range from 0 to 30° C., and a pH value of about 3.0 to 5.0. In the precipitation tank 15, KHT will at least partly crystallize. The crystal-containing suspension formed is supplied through line 17 to a filter 18, preferably a band filter, which is charged with washing water that comes from line 19. Used washing water is withdrawn via line 20, and it can be used in a manner not represented for instance in the yeast washing 7.

The moist KHT crystals obtained in the filter 18 are charged through line 21 to a stirred tank 22, which is likewise provided with a heating jacket 22a. In the tank 22, the crystals are expediently dissolved at temperatures of 70 to 95° C. in water which is supplied via line 23. Through line 24, tartaric acid solution is at the same time supplied to the tank 22. A largely saturated KHT solution is withdrawn from the stirred tank via line 25 and is first of all passed through a decoloration treatment 29, for instance an activated carbon bed, and then through the cation exchanger 26 which binds the K+ions. In this way a largely purified tartaric acid solution is produced, which apart from water usually comprises 10 to 20 wt-% tartaric acid. This solution is withdrawn via line 27, a part thereof is recirculated to the tank 22 via line 24, and the remaining tartaric acid solution is withdrawn through line 28. When the cation exchanger 26 is loaded, it is regenerated for instance with sulfuric acid or hydrochloric acid, as it is known and common practice.

If a highly purified tartaric acid is desired, the solution of line 28 is also passed through an anion exchanger 30, which in the initial state is loaded with tartaric acid. This anion exchanger binds residual anions, for instance sulfate or chloride ions. The tartaric acid solution flows through line 28 to a conventional evaporation 35, in order to remove water. The aqueous condensate formed is withdrawn via line 32 and recirculated through lines 19 and 23, as has already been explained. From the evaporation there is obtained a tartaric acid solution which usually comprises 50 to 60 wt-% tartaric acid and is withdrawn via line 33. A partial stream of this solution, which is branched off via line 34, may be recirculated to line 16 and be charged into the precipitation tank 15. The remaining solution is charged into a likewise conventional crystallization 37, and crystallized tartaric acid is withdrawn via line 36. A washing, drying and grinding of this tartaric acid from line 36 may follow, which was, however, not represented for simplification.

In an alternative to the explained procedure, the cation exchanger 26 is replaced by an electrolysis known per se, which electrolytically breaks down the KHT solution from line 25 into a tartaric acid solution and a KOH solution upon reaction with KOH to form a DKT solution. The KOH solution obtained may at least partly be recirculated to the stirred tank 2. The tartaric acid solution produced is obtained in line 27 and is subjected to a further treatment as described above.

EXAMPLE

On a laboratory scale, yeast from the wine production with a KHT content of 10 wt-% is intensively mixed in the tank 2 per kg with 2.5 kg water and aqueous KOH solution (10 wt-% KOH), where the temperature is about 70° C. The weight ratio of the additions of total water and yeast is 2.7:1, by means of the KOH solution the pH value of the suspension is adjusted to 8.0. To achieve the complete conversion from KHT to DKT, stirring is performed for 1 hour.

In a ceramic microfiltration 5, the solids are separated from the suspension at a transmembrane pressure of 6 bar at 70° C., where a filter cake with 30 wt-% dry matter is obtained. The permeate of the filtration, the particle-free DKT solution, has a DKT content of 10 wt%. This permeate is cooled to 15° C. and then mixed by stirring in the container 15 with so much pure tartaric acid until a pH value of 3.5 is achieved. There is obtained a saturated KHT solution, where at the same time crystalline KHT is precipitated.

The filtered KHT crystals are repeatedly washed with distilled water and then heated to 80° C. in the tank 22, where a saturated KHT solution with 44 g/l KHT is obtained. The crystal-free saturated solution is passed over an activated carbon column 29 and thereby decolorized. For removing the potassium ions the decolorized solution is passed over a strongly acid cation exchanger 26 and there is obtained a purified aqueous tartaric acid solution, which is suited for concentration, evaporation and crystallization in a manner known per se.

We claim:

1. A process of producing tartaric acid from a raw material whose dry matter comprises at least 5 wt-% potassium hydrogentartrate (KHT), wherein
    a) in a first reaction stage the raw material is mixed with aqueous potassium hydroxide solution, and KHT is virtually completely reacted to form dipotassium tartrate (DKT),
    b) from the first reaction stage there is withdrawn a first aqueous solution containing DKT, impurities are removed, and in a precipitation stage the first solution is mixed with added acid at a pH value of 2.0 to 5.0, and a suspension containing crystallized KHT is produced,
    c) crystallized KHT is separated from the suspension, washed with water, and there is produced a second aqueous solution saturated with KHT for at least 80 wt-%, and
    d) from the second aqueous solution potassium is removed, an aqueous tartaric acid solution is produced, and from the tartaric acid solution water is at least partly removed.

2. The process as claimed in claim 1, wherein a yeast-containing raw material is charged to the first reaction stage a), from the first stage there is withdrawn a first solution containing DKT and yeast, and from the first solution a yeast-containing sludge is separated.

3. The process as claimed in claim 1, wherein tartaric acid is added to the precipitation stage.

4. The process as claimed in claim 1, wherein in stage d), the second aqueous solution is passed through a cation exchanger, where $K^+$ ions are bound.

5. The process as claimed in claim 1, wherein in stage d), the second aqueous solution is reacted with KOH to obtain a DKT solution, and this solution is charged to an electrolysis, from which a tartaric acid solution and, separate therefrom, a KOH solution is withdrawn.

6. The process as claimed in claim 1, wherein before water is at least partly removed, the tartaric acid solution is passed through an anion exchanger initially loaded with tartaric acid.

* * * * *